US00PP34130P2

(12) United States Plant Patent
Hansen

(10) Patent No.: US PP34,130 P2
(45) Date of Patent: Apr. 12, 2022

(54) ***MONARDA* PLANT NAMED 'LEADING LADY RAZZBERRY'**

(50) Latin Name: ***Monarda* hybrid**
Varietal Denomination: Leading Lady Razzberry

(71) Applicant: Hans A Hansen, Zeeland, MI (US)

(72) Inventor: Hans A Hansen, Zeeland, MI (US)

(73) Assignee: Walters Gardens, Inc, Zeeland, MI (US)

( * ) Notice: Subject to any disclaimer, the term of this patent is extended or adjusted under 35 U.S.C. 154(b) by 0 days.

(21) Appl. No.: 17/300,860

(22) Filed: Nov. 29, 2021

(51) Int. Cl.
*A01H 5/02* (2018.01)
*A01H 6/50* (2018.01)

(52) U.S. Cl.
USPC ..... Plt./455
CPC ..... *A01H 6/50* (2018.05)

(58) Field of Classification Search
USPC ..... Plt./455
CPC ..... A01H 5/02
See application file for complete search history.

*Primary Examiner* — Kent L Bell

(57) ABSTRACT

The new and distinct cultivar of ornamental cultivar of hybrid ornamental Bee Balm plant named *Monarda* 'Leading Lady Razzberry' with deep-green, moderately-glossy, powdery mildew-tolerant foliage, dense flower heads nearly completely covering the plant in peak bloom with bright, raspberry-purple flowers with darker purplish-red spots. The plant habit is short, compact and winter-hardy, making the new plant useful in the landscape as a specimen, en masse, or as a containerized plant.

1 Drawing Sheet

Botanical designation and cultivar denomination:
Botanical classification: *Monarda* hybrid.
Variety denomination: 'Leading Lady Razzberry'.

STATEMENT REGARDING PRIOR DISCLOSURES UNDER 37 CFR 1.77(B)(6)

The first non-enabling disclosure of the claimed plant was on Dec. 1, 2020 the claimed plant was displayed with a non-enabling photograph and brief description in a website operated by Walters Gardens, Inc., and on May 21, 2021 as a non-enabling photograph and brief description in the 2021-2022 Catalog by Walters Gardens, Inc., who obtained the plant and all information relating thereto, from the inventor. The first sales of the new plant were on May 3, 2021 from Walters Gardens, Inc. to Chrissy's Greenhouse and Home Nursery. No plants of *Monarda* 'Leading Lady Razzberry' have been sold, in this country or anywhere in the world, nor has any disclosure of the new plant been made more than one year prior the filing date of this application, and such sale or disclosure within one year was either derived directly or indirectly from the inventor.

BACKGROUND OF THE INVENTION

The present invention relates to the new and distinct cultivar of Bee Balm, botanically known as *Monarda* 'Leading Lady Razzberry', and hereinafter also referred to solely by the cultivar 'Leading Lady Razzberry' or the "new plant." *Monarda* 'Leading Lady Razzberry' was the result of a controlled pollination in the summer of Jul. 24, 2014 in trial garden at a wholesale perennial nursery in Zeeland, Mich., USA. The female parent is a proprietary, unnamed, unreleased hybrid known as 12-21-4 (not patented) and the specific male parent is a proprietary, unnamed, unreleased hybrid known as 12-59-7 (not patented). The new plant was separated out for further evaluation in the summer of 2016 in the full sun trial gardens of the same nursery and assigned the breeder code 14-08-1. The new plant is the result of a planned breeding program of the inventor to produce new colors of flowers with increased mildew resistance and improved compact habit. The new plant has been asexually propagated since 2016 by division and by basal stem cuttings at the same nursery in the greenhouses in Zeeland, Mich., and the subsequent generations of asexually propagated plants found to be stable and identical to the original selection.

BRIEF SUMMARY OF THE PLANT

*Monarda* 'Leading Lady Razzberry' is unique from its parents and all other Bee Balm plants known to the inventor. The nearest comparison cultivars known to the inventor are: 'Pardon My Cerise' U.S. Plant Pat. No. 9,234 'Pardon My Purple' U.S. Plant Pat. No. 22,170, 'Cherry Pops' U.S. Plant Pat. No. 27,618 and 'Leading Lady Pink' U.S. Plant patent application Ser. No. 17/300,361, copending.

'Pardon My Cerise' has deeper cherry-red flowers and the habit is slightly taller. 'Pardon My Purple' has flowers of a fuchsia-purple color and is slightly taller in habit. 'Cherry Pops' has a taller habit and the flower color is cherry-red. 'Leading Lady Razzberry' flowers earlier than the three above listed comparison cultivars. 'Leading Lady Pink' has a similar habit and flowering period, but the flowers are bright pink with lighter interiors that show off the darker purplish-red spotting. The leaves of 'Pardon My Cerise' and 'Cherry Pops' are slightly wider.

The female parent is more open and taller in habit and later to flower than the new plant and darker pink in flower color. The male parent has a shorter habit and the flowers are more purple-colored.

*Monarda* 'Leading Lady Razzberry' is distinct from all Bee Balm plants known to the inventor. The following are traits of the new plant that in combination distinguish it from all other Bee Balm known to the inventor:

1. Short, compact, clumping, upright mound that is winter-hardy habit;
2. Deep-green, moderately-glossy, powdery mildew-tolerant foliage;
3. Leaves and bracts below the flowers develop a purplish cast;
4. Compact, bright, raspberry-purple flowers with darker purplish-red spots;
5. Flowering over a five-week-long period beginning early June;
6. Flowering in dense verticils that nearly completely cover the plant in peak bloom.

BRIEF DESCRIPTION OF THE DRAWINGS

The photographs of the new plant demonstrate the unique traits of *Monarda* 'Leading Lady Razzberry' and the overall appearance of the plant at a nursery in Zeeland, Mich. The colors are as accurate as reasonably possible with color reproductions. Variation in ambient light spectrum, source and direction may cause the appearance of minor variation in color.

DETAILED BOTANICAL DESCRIPTION

Figure 1:
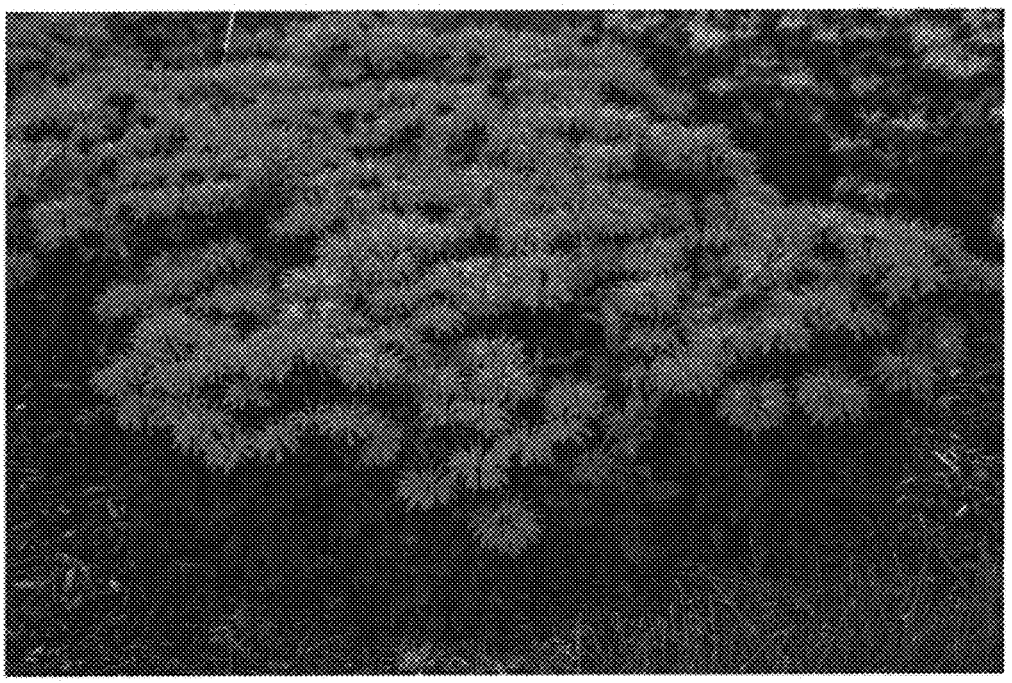
FIG. 1 shows the habit of the new plant in full flower at three-years-old in the full sun trial garden.
Figure 2:
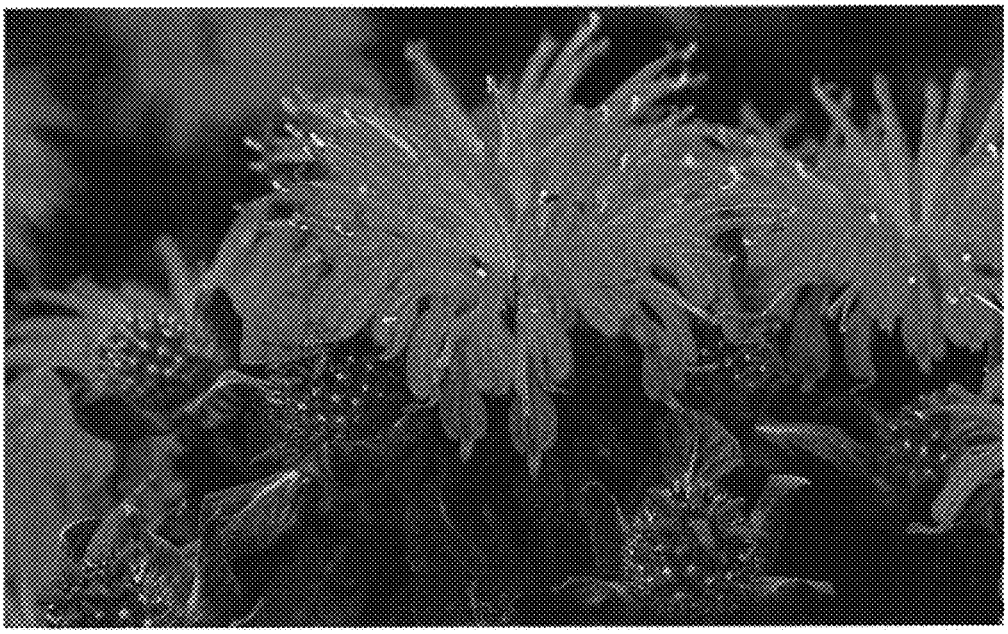
FIG. 2 shows a close-up of the flower and buds of two-year-old plant in a partially shaded greenhouse.

The following descriptions and color references are based on the 2015 edition of The Royal Horticultural Society Colour Chart except where common dictionary terms are used. *Monarda* 'Leading Lady Razzberry' has not been observed under all possible environments. The phenotype may vary slightly with different growing environments such as temperature, light, fertility, soil pH, moisture and maturity levels, but without any change in the genotype. The following observations and size descriptions are based on two and three-year-old plants grown in a trial garden at a nursery in Zeeland, Mich. with supplemental fertilizer and water as needed.

Botanical classification: *Monarda* hybrid;

Parentage: The female (seed) parent is 12-21-4, an unreleased proprietary hybrid; the male (pollen) parent is 12-59-7, an unreleased, proprietary hybrid;

Plant habit: Hardy herbaceous perennial, dense, upright mound, producing multiple stems spreading by short rhizomes near the base of the stems; foliage up to 30.0 cm tall, flowering to 35.0 cm tall and 60.0 cm wide; flowering begins late spring in Michigan and continues for about 5 weeks;

Propagation: Stem cuttings;

Time to produce finished crop in 3.8-liter pots: About 7 to 9 weeks; moderate rate of growth;

Root: Fine, fibrous and freely branching; color creamy white to tan depending on soil type;

Leaves: Simple; lanceolate; opposite; margin serrated and ciliolate; puberulent above and below; moderately lustrous adaxial, matte to slightly lustrous abaxial; narrowly acute apex; cordate to rounded base; to about 5.7 cm long and 3.2 cm wide, average about 4.8 cm long and 2.1 cm wide near base;

Leaf color: Young expanding leaves adaxial between RHS 138A and RHS 138B with a blush of nearest RHS 187B around edges, abaxial nearest RHS 146B with moderate to strong blush of nearest RHS 187B; mature leaves adaxial nearest RHS 139A with slight anthocyanins blush of nearest RHS 187A in the distal leaves, abaxial nearest RHS 147B with slight to moderate anthocyanins blush of nearest RHS 187B in the distal leaves;

Foliage fragrance: Pleasant lemony-herbal;

Veins: Pinnate; glabrous and slightly sunken adaxial, micro-pubescent and costate abaxial;

Vein color: Adaxial midrib nearest RHS 145C and lateral pinnate veins and secondary veins RHS 145B near center and distally nearest RHS 138B, with increasing blush on midrib and veins of nearest RHS N186C with increased ultraviolet exposure; abaxial midrib variable, nearest RHS 145C and lateral pinnate veins nearest RHS 147C and secondary veins nearest RHS 137B;

Petiole: Micro-puberulent, slightly concaved above; to about 4.0 mm long and 3.3 mm across at base, shorter distally;

Petiole color: Adaxial nearest RHS 146C and abaxial nearest RHS 146D with slight anthocyanin blush of nearest RHS 187B;

Stems: Quadrangular; puberulent; about 4.0 mm across at base; about 60 per plant; naturally branched at upper nodes; average 2.7 cm between nodes, greater distally; 9 to 11 nodes per stem; average length about 30 cm;

Stem color: Nearest RHS 147D with anthocyanin expression increasing distally to moderate blush of nearest N186C; nodes same color as surrounding stem;

Flowers: Single, bilabiate flowers arranged in mostly terminal verticils forming globular head inflorescence about 74.0 mm across and 40.0 mm tall, opening from the center and progressing outwardly and down; attitude outwardly to upwardly; individual flowers to about 38.0 mm long to exserted stigma, corolla to about 36.0 mm long, 16.0 mm tall and about 5.0 mm across; individual flowers persisting about 5 days in Michigan; numerous, about 150 to 200 flowers per terminal head, fewer per axillary head; 80 inflorescences with open flowers at one time;

Flower fragrance: Moderately spicy;

Buds one to two days prior to opening: Narrowly oblanceolate, arcuate downward; about 28.0 mm long and 3.0 mm across and 5.5 mm tall;

Bud color: Basal 2.0 mm nearest RHS 155C, distal portion nearest RHS 71A;

Petals: Bilabiate; arcuate downward; basal 20.0 mm fused into tube; split in two in the distal 16.0 mm; abaxial glandular to puberulent, adaxial glabrous; self-cleaning;

Upper labium: Folded in middle and distal regions, about 15.0 mm long from fusion to acute apex, 3.0 mm tall and 3.0 mm across above fusion;

Lower labium: About 17.0 mm long from fusion to apex, apex comprising three lobes including two side lobes about 1.0 mm long and 2.0 mm across with rounded apex; center lobe bent upwardly at base, about 5.0 mm long with emarginate apex in the distal 0.5 mm; main portion with darker spots between 0.5 mm and 1.2 mm across;

Petal color: Upper labium adaxial surface between RHS 63A and RHS 63B, abaxial between RHS 61A and RHS 61B; lower labium adaxial surface nearest RHS 61B with spots nearest RHS 61A, abaxial nearest RHS 61B with spots showing through from adaxial surface of nearest RHS 61A; corolla adaxial tube proximal 5.0 mm nearest RHS NN155C and distally nearest RHS 63B, abaxial tube proximal 5.0 mm between RHS 155D and RHS NN155B and distal portion nearest RHS 64B and lightening to nearest RHS 63C before dropping;

Androecium: Two; adnate inner corolla tube in basal portion;

*Filaments*.—Two; distally curved downward; adnate to the inner corolla tube in the basal 18.0 mm and free in the distal 18.0 mm; about 0.5 mm diameter; color in free portion between RHS 70B and RHS 71C, color in adnate portion nearest RHS 69B.

*Anther*.—Oblong elliptic; dorsifixed; longitudinal; fused together; 3.0 mm long by 1.0 mm wide; color nearest RHS 72A.

*Pollen*.—Abundant, elliptic to globose, less than 0.1 mm; color nearest RHS NN155A.

Gynoecium: One; superior; about 37.0 mm long; exserted about 2.0 mm beyond upper labium when mature;

Style: Cylindrical; glabrous; about 33.0 mm long and about 0.3 mm diameter; arcuate along upper labium; color nearest RHS 64A in distal 5.0 mm transitioning to nearest RHS NN155D in middle and basal portion;

Stigma: Unevenly bifid in the distal 1.5 mm and about 0.2 mm in diameter; color nearest RHS 64A;

Ovary: Conical; about 1.0 mm tall by 0.75 mm diameter; color nearest RHS 145D;

Calyx: Tubular to campanulate; consisting of five fused sepals; about 8.5 mm long and 2.0 mm diameter at apex;

Sepals: Five; narrowly acute apex; fused in basal 7.0 mm forming calyx tube adpressed to corolla tube, free in distal 1.5 mm; margin micro-serrulate; about 8.5 mm long and 1.0 mm across at fusion; glabrous adaxial and abaxial; persistent;

Sepal color: Adaxial and abaxial basal 2.0 mm nearest RHS 145D, middle adaxial portion nearest RHS 145B with veins nearest RHS 146C, middle abaxial portion nearest RHS 146D with veins nearest RHS 146C; adaxial and abaxial free portion between RHS N186A and RHS N186B;

Foliar bracts: Typically two sets of five to seven large bracts below inflorescence; proximal set deltoid, distal set lanceolate; apex narrowly acute; base sessile and truncate; margin entire and micro-ciliolate; glabrous adaxial, puberulent abaxial; mostly flat; proximal set about 16.0 mm long and 12.0 mm wide, distal set about 11.0 mm long and 4.0 mm wide;

Foliar bract color: Both sets similar, adaxial and abaxial tube portion nearest RHS 137A with moderate to strong blushing of nearest RHS N186C;

Peduncle: Pubescent, stiff, strong, erect, quadrangular; to about 3.0 mm across above leaves and average 40.0 mm long above the last set of leaves; about 80 per plant at one time; naturally branched at nodes;

Peduncle color: RHS 147A with moderate to heavy blush of RHS N186C;

Pedicel: About 2.0 mm long and 0.8 mm diameter; color nearest RHS 145B;

Fruit: Single, glabrous, lustrous, ellipsoidal nutlet; about 1.2 mm long and 0.7 mm wide; color nearest RHS 200C;

Hardiness: The new plant grows best with plenty of moisture and adequate drainage; hardy to at least from USDA zone 4 through 8.

Disease and pest resistance: Demonstrated greater than average powdery mildew tolerance in side-by-side comparison with other *Monarda*.

I claim:

1. A new and distinct hybrid ornamental Bee Balm plant named *Monarda* 'Leading Lady Razzberry', as herein described and illustrated.

* * * * *